(12) United States Patent
Habu et al.

(10) Patent No.: US 8,643,838 B2
(45) Date of Patent: Feb. 4, 2014

(54) EMISSION SPECTROPHOTOMETER

(75) Inventors: Toshiya Habu, Kyoto (JP); Eizo Kawato, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 13/050,701

(22) Filed: Mar. 17, 2011

(65) Prior Publication Data

US 2011/0235033 A1    Sep. 29, 2011

(30) Foreign Application Priority Data

Mar. 25, 2010 (JP) ................................ 2010-070364

(51) Int. Cl.
| | | |
|---|---|---|
| *G01J 3/42* | (2006.01) | |
| *G01J 3/30* | (2006.01) | |
| *G01J 3/28* | (2006.01) | |
| *G01J 3/44* | (2006.01) | |
| *G01J 1/58* | (2006.01) | |
| *G01R 27/26* | (2006.01) | |

(52) U.S. Cl.
USPC ........... 356/319; 356/301; 356/313; 356/317; 356/318; 356/326; 250/458.1; 324/672; 324/676; 324/677; 324/678

(58) Field of Classification Search
USPC .................................. 356/313; 324/657–690
See application file for complete search history.

(56) References Cited

U.S. PATENT DOCUMENTS

| | | | |
|---|---|---|---|
| 3,906,291 A | * | 9/1975 | Schayes et al. ............... 315/171 |
| 2010/0073844 A1 | * | 3/2010 | Osa ............................... 361/263 |
| 2010/0208255 A1 | * | 8/2010 | Osa ............................... 356/313 |

FOREIGN PATENT DOCUMENTS

| | | | | |
|---|---|---|---|---|
| CN | 101558291 A | | 10/2009 | |
| JP | 08-145891 | | 6/1996 | |
| WO | WO 2008/072318 | * | 6/2008 | ..................... 356/313 |
| WO | WO 2009/031180 | * | 12/2009 | ..................... 356/313 |

OTHER PUBLICATIONS

"First Office Action of China Counterpart Application", issued on Jan. 16, 2013, with English translation thereof, p1-p12, in which the listed reference was cited.
"Office Action of Japan Counterpart Application", with English translation thereof, mailed on Nov. 19, 2013, P1-P6.

* cited by examiner

*Primary Examiner* — Tarifur Chowdhury
*Assistant Examiner* — Sunghee Y Gray
(74) *Attorney, Agent, or Firm* — J.C. Patents

(57) ABSTRACT

An emission spectrophotometer capable of inhibiting non-uniformity of spectral intensities of component elements is provided. The emission spectrophotometer generates pulse light emission by supplying an energy accumulated in an electricity accumulating and discharging unit to a gap between an electrode and a test material, and the emission spectrophotometer includes a detection unit, for detecting an energy charged to the electricity accumulating and discharging unit before the pulse light emission; and a detection unit, for detecting an energy remaining in the electricity accumulating and discharging unit after the pulse light emission. It is determined whether the detected light is emitted by fully using the energy accumulated in the electricity accumulating and discharging unit.

3 Claims, 4 Drawing Sheets

EMISSION SPECTROPHOTOMETER

CROSS-REFERENCE TO RELATED APPLICATION

This application claims the priority benefit of Japan patent application serial no. 2010-070364, filed on Mar. 25, 2010. The entirety of the above-mentioned patent application is hereby incorporated by reference herein and made a part of the specification.

BACKGROUND OF THE INVENTION

1. Field of the Invention

The present invention generally relates to an emission spectrophotometer for enabling a solid test material to generate pulse light emission to analyze element content, in particular, to a power supply device of the emission spectrophotometer.

2. Description of Related Art

Generally, during an analysis of a solid test material in an emission spectrophotometer, spark discharge is generally generated between an electrode 7 and a test material 8 by a power supply device 1, as shown in FIG. 1. Then, an emitted light is split into spectrum lights of component elements by using a light splitter 9, the spectrum lights are incident to photomultipliers 10a-10e mounted at positions corresponding to spectrum wavelengths intrinsic to the component elements, and output currents of the photomultipliers are integrated by using detection circuits 11a-11e, such that a spectral intensity of each component element is calculated.

Herein, as each spectral intensity is proportional to the content of each component element, a data processing device 12 converts the spectral intensity of each component element into the content. However, the spark discharge is not always generated in an identical state, and thus non-uniformity is resulted due to the differences of the surface state of the test material, the front end shape and the surface state of the electrode, or the state of the Ar gaseous environment. That is to say, when pinholes or fine cracks exist in the test material, or when the front end shape or the surface state of the electrode is changed due to the adhesion or the fusing of the evaporated material from the test material, or when the purity or the flow quantity of Ar is changed, the state of spark discharge is correspondingly changed, thereby causing the non-uniformity of the spectral intensities of the component elements obtained when the pulse light emission is generated by the test material. Therefore, as described in Patent Document 1, in the prior art, the data processing device 12 eliminates the data when the spectral intensity departs from a normal intensity range and becomes extremely high or low by using the method described below.

In the case of analyzing a solid test material, pulse light emission is generated first, a spectrum light of each component element is detected, and data of a group of spectral intensities as shown in FIG. 5 is stored in a memory device. A histogram of the group of spectral intensities correlating with a main component element as shown in FIG. 6 is plotted based on the data stored in the memory device. For example, if the test material is a steel test material, a histogram of a group of spectral intensities correlating with a main component element Fe is plotted. Then, an average value $I_{AV}$ and a standard deviation $\sigma$ when the histogram is considered to have a normal distribution are calculated, according to the average value $I_{AV}$ and the standard deviation $\sigma$, a pair of upper and lower spectral intensities $I_{AV} \pm k\sigma$ (k is a constant) with the average value $I_{AV}$ as a center and determined by the standard deviation $\sigma$ are set as the threshold. Finally, as for the data of the group of spectral intensities of the component elements stored in the memory device, only the data of the spectral intensity of the main component element which is in the preset threshold range is valid, and the data departing from the threshold range is excluded.

Furthermore, in the prior art, a control circuit 2 of the power supply device 1 of the emission spectrophotometer controls a charging circuit 3, such that an energy set by the data processing device 12 is charged to an electricity accumulating and discharging unit (for example, a condenser) 4. Then, a high voltage transformer drives a circuit 5 to work, such that the high voltage transformer 6 generates a high voltage, and insulation breakdown occurs thereafter between the electrode and the test material. As a result, the energy charged to the electricity accumulating and discharging unit 4 is supplied to the gap between the electrode and the test material.

PRIOR ART DOCUMENT

Patent Document

[Patent Document 1] Japanese Patent Publication No. H. 8-145891

For the prior art, when the state of the spark discharge is greatly changed, and the spectral intensity of the main component element departs from a normal intensity range and becomes extremely high or low, the data obtained in this case can be easily excluded. However, when a threshold set range of a pair of upper and lower spectral intensities with the average value of the histogram of the group of spectral intensities of the main component element as a center is wide, the non-uniformity among the states of the spark discharge of the obtained data is large, such that the error of the spectral intensities of all the component elements is high.

In addition, when the threshold set range of the pair of upper and lower spectral intensities with the average value of the histogram of the group of spectral intensities of the main component element as the center is narrow, the reproducibility of the spectral intensities of all the component elements is poor because few data is obtained. In addition, the influence of the state of the spark discharge on the spectral intensity varies with each component element. Thus, if only a threshold is set with respect to the spectral intensity of the main component element, and the data departing from the threshold is excluded, the non-uniformity of the spectral intensities of all the component elements cannot be fully inhibited.

SUMMARY OF THE INVENTION

In order to solve the above problems, the present invention is directed to an emission spectrophotometer, which generates pulse light emission by supplying an energy accumulated in an electricity accumulating and discharging unit to a gap between an electrode and a test material, and includes a detection unit, for detecting an energy charged to the electricity accumulating and discharging unit before the pulse light emission; and a detection unit, for detecting an energy remaining in the electricity accumulating and discharging unit after the pulse light emission.

In the structure, a power supply device calculates a difference between the charged energy detected before the pulse light emission and the remaining energy detected after the pulse light emission, such that the energy supplied to the gap between the electrode and the test material in spark discharge is detected.

In addition, the emission spectrophotometer includes a comparison unit, for comparing the charged energy detected before the pulse light emission with a preset threshold.

In addition, the emission spectrophotometer includes a comparison unit, for comparing the remaining energy detected after the pulse light emission with a preset threshold.

Moreover, if the charged energy detected before the pulse light emission is in the preset threshold range, and the remaining energy detected after the pulse light emission is in the preset threshold range, normal discharge is determined; and if the charged energy and the remaining energy are beyond the preset threshold range, abnormal discharge is determined.

EFFECT OF INVENTION

According to the present invention, only the data of the spectral intensity in the spark discharge with an energy in a specified range can be obtained, in which the energy is obtained by subtracting the energy, remaining in the electricity accumulating and discharging unit after the pulse light emission, from the energy charged to the electricity accumulating and discharging unit before the pulse light emission, that is, the remaining energy is supplied between the electrode and the test material in the spark discharge. Because only the spectral intensity data of the spectral discharge which is in a specified range can be obtained, the non-uniformity of the energy supplied to the gap between the electrode and the test material is lowered among the obtained data, so the error between the spectral intensities of all component elements is inhibited to a lower level.

Additionally, analysis is performed until the number of times of the spark discharge with an energy in the preset threshold range reaches a preset number, wherein the energy is obtained by subtracting the energy, remaining in the electricity accumulating and discharging unit after the pulse light emission, from the energy charged to the electricity accumulating and discharging unit before the pulse light emission. Therefore, the obtainable data amount is always kept constant, and thus the reproducibility of the spectral intensities of all component elements is improved.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIGS. 4(a) and 4(b) show practically detected data of a voltage at two ends of a condenser and a discharging current, in which FIG. 4(a) shows practically detected data in normal discharge, and FIG. 4(b) shows practically detected data in abnormal discharge.

DESCRIPTION OF THE EMBODIMENTS

Figure 1:
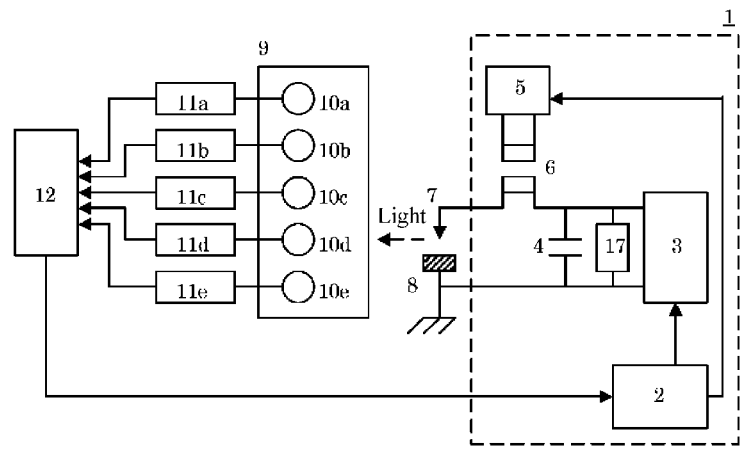
FIG. 1 is a block diagram of a structure of a power supply device of an emission spectrophotometer in the prior art.

Reference will now be made in detail to the present embodiments of the invention, examples of which are illustrated in the accompanying drawings. Wherever possible, the same reference numbers are used in the drawings and the description so as to refer to the same or like parts.

Figure 2:
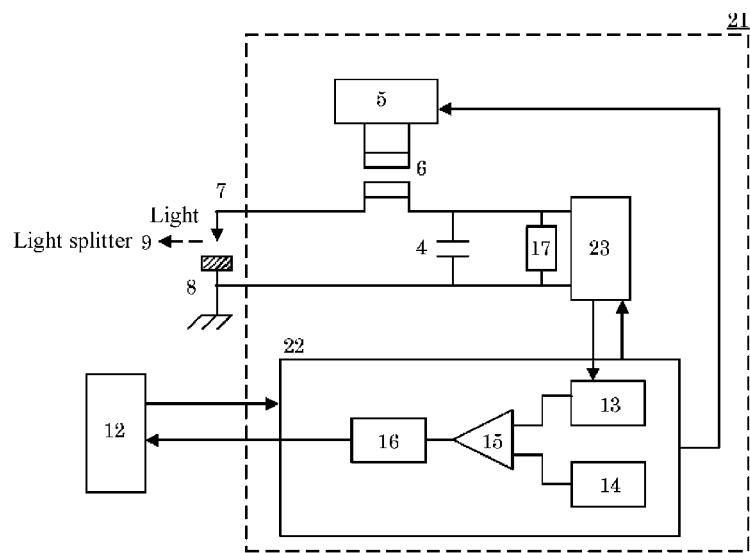
FIG. 2 is a block diagram of a structure of a power supply device of an emission spectrophotometer according to an example of the present invention.

FIG. 2 is a block diagram of a structure of an emission spectrophotometer according to an example of the present invention. In FIG. 2, a control circuit 22 of a power supply device 21 controls a charging circuit 23, such that an energy set by a data processing device 12 is charged to an electricity accumulating and discharging unit 4, and a high voltage transformer drives a circuit 5 to function, such that the high voltage transformer 6 generates a high voltage, and then insulation breakdown occurs between an electrode 7 and a test material 8. As a result, the energy charged to the electricity accumulating and discharging unit 4 is supplied to a gap between the electrode 7 and the test material 8. So far, the structure is the same as that of the emission spectrophotometer in the prior art.

The power supply device of the present invention has a specific structure, in which an energy detection circuit 13 is used to detect both the energy charged to the electricity accumulating and discharging unit before pulse light emission, and the energy remaining in the electricity accumulating and discharging unit after the pulse light emission. The two energies are compared with outputs from a threshold setting circuit 14 in a comparison circuit 15, and an output circuit 16 outputs a comparison result to the data processing device 12. The energy detection circuit 13 for detecting the energy in the electricity accumulating and discharging unit 4 is set, for example, as a circuit for detecting a voltage at two ends of a condenser in the case that the electricity accumulating and discharging unit 4 is the condenser.

EXAMPLE

Figure 3:
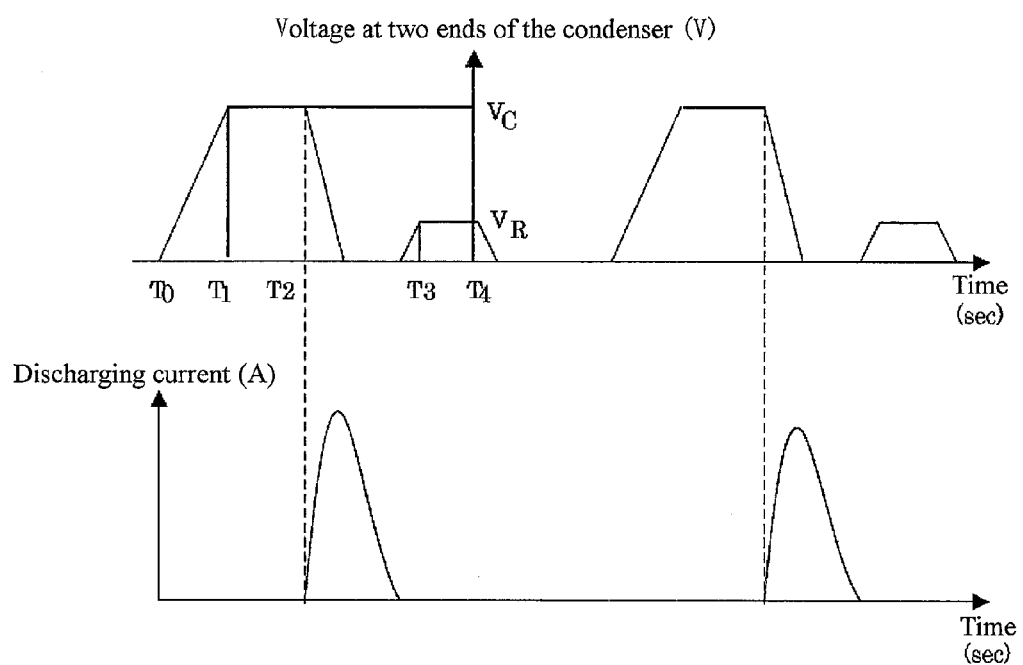
FIG. 3 is an illustration view of a wave form of a voltage at two ends of a condenser and a discharging current.

FIG. 3 is an illustration view of a wave form of a voltage at two ends of a condenser and a discharging current in two times of spark discharge. In FIG. 3, the charging circuit 23 as shown in FIG. 2 charges the energy to the condenser 4 from time $T_0$ to time $T_1$, and the energy detection circuit 13 as shown in FIG. 2 detects a voltage $V_C$ at two ends of the condenser from time $T_1$ to time $T_2$. The high voltage transformer as shown in FIG. 2 drives the circuit 4 to work at time $T_2$. The high voltage transformer 5 generates a high voltage, insulation breakdown occurs between the electrode 7 and the test material 8, and a discharging current begins to flow.

Then, the voltage at two ends of the condenser 4 temporarily drops to 0 V, and the energy accumulated in the condenser 4 is supplied to the gap between the electrode 7 and the test material 8, and to a winding wire of the high voltage transformer 6. After the voltage at two ends of the condenser 4 reaches 0 V, the discharging current returns in a diode 17; thus, the voltage at two ends of the condenser 4 reaches a fixed value. Experiments indicate that if all the charged energy in the condenser 4 is supplied to the gap between the electrode 7 and the test material 8, the voltage at two ends of the condenser 4 is not increased any more; however, in an abnormal discharge, not all the charged energy in the condenser 4 is supplied to the gap between the electrode 7 and the test material 8, and a part of the charged energy returns and remains in the condenser 4.

From time $T_3$ to $T_4$, the energy detection circuit 13 as shown in FIG. 2 detects the voltage $V_R$ remaining in the condenser. At time $T_4$, a reset circuit inside the power supply device works, to discharge the energy remaining in the condenser; thus, the voltage at two ends of the condenser returns to the initial state. Herein, the reset circuit is set, for example, as a circuit which connects a switch closed at time $T_4$ and a resistor at the two ends of the condenser.

Figure 4A:
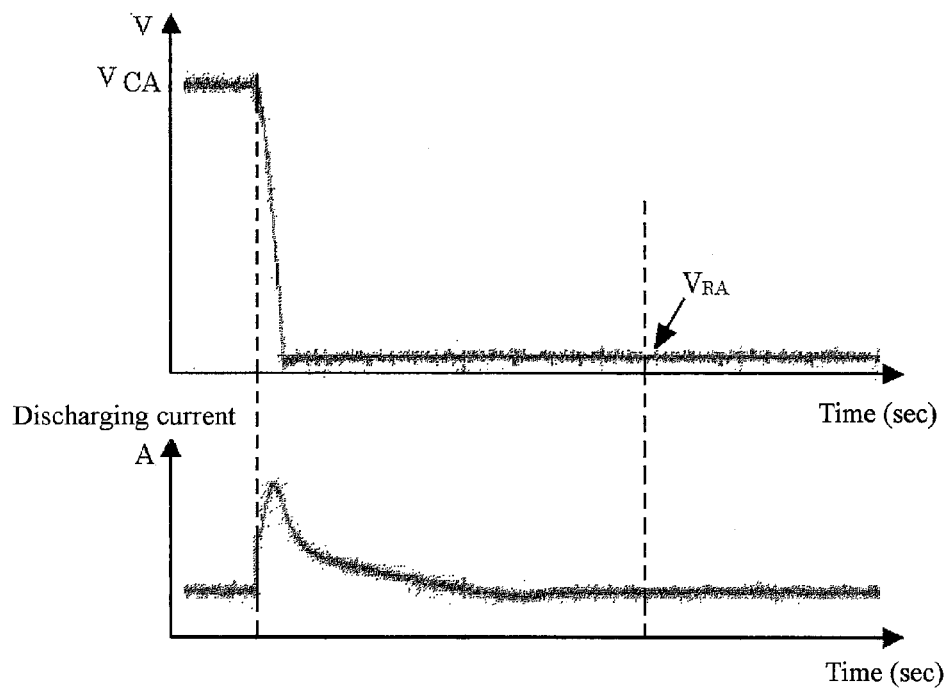
Figure 4B:
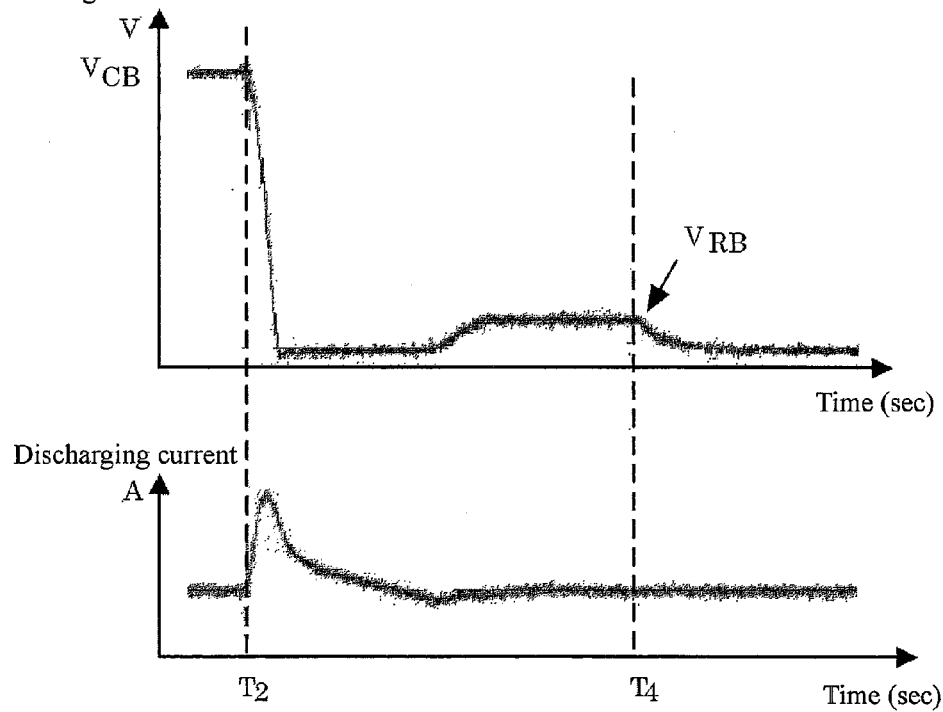
Figure 5:
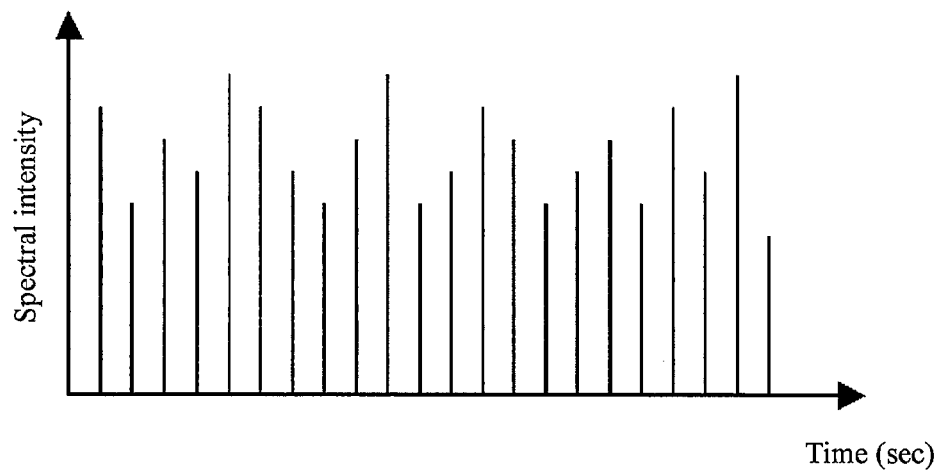
FIG. 5 is an illustration view of data of a group of spectral intensities of component elements obtained by an emission spectrophotometer.
Figure 6:
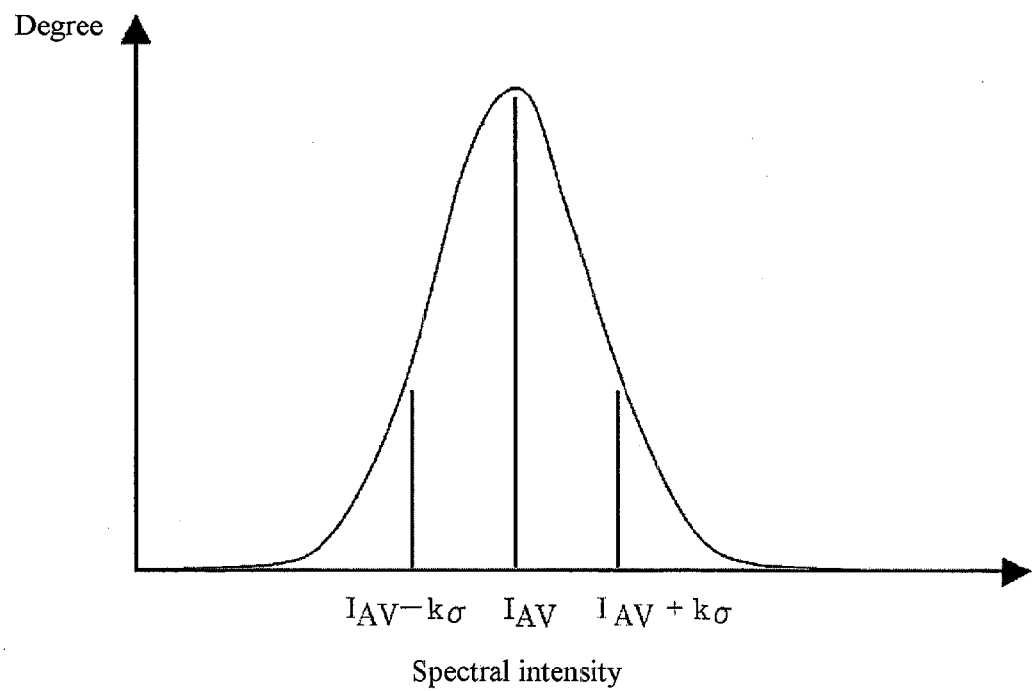
FIG. 6 is an illustration view of a histogram of main component elements based on the group of spectral intensities as shown in FIG. 5.

Then, the practically detected wave form of the voltage at two ends of the condenser and the discharging current is shown in FIGS. 4(a) and 4(b). The charging voltage $V_{CA}$ in FIG. 4(a) is equivalent to the charging voltage $V_{CB}$ in FIG. 4(b), but the remaining voltage $V_{RA}$ in FIG. 4(a) is lower than the remaining voltage $V_{RB}$ in FIG. 4(b). If the threshold setting circuit 14 as shown in FIG. 2 sets the threshold between $V_{RA}$ and $V_{RB}$, the case in FIG. 4(a) is determined to be normal discharge and the case in FIG. 4(b) is determined to be abnormal discharge.

Furthermore, in the case that the electricity accumulating and discharging unit is a condenser, the energy detection circuit 13 as shown in FIG. 2 is set as a circuit for detecting a value or an integrated value of the current flowing from the charging circuit 23 into the condenser 4 when detecting the discharged energy of the condenser. Moreover, the energy detection circuit 13 may be further set as a circuit for detecting a value or an integrated value of the current flowing from the condenser to the reset circuit when detecting the remaining energy in the condenser. Furthermore, the threshold setting circuit 14 as shown in FIG. 2 may be set as a circuit using a voltage fixing element to generate a fixed voltage, or set as a circuit generating a voltage corresponding to the setting of the data processing device 12, for example, a Digital Analog (DA) conversion circuit, which generates, for example, different voltages, depending on the difference of the charged energy.

The data processing device 12 only obtains the spectral intensity in the spark discharge with the charged energy and the remaining energy, detected by the energy detection circuit 13, in the threshold range set by the threshold setting circuit 14, according to the output from the output circuit 16. In addition, the data processing device 12 may make the power supply device 1 work for the number of times of the preset discharging, or make the power supply device 1 work until the number of times of the spark discharge reaches the preset number of times, wherein the charged energy and the remaining energy of the spark detected by the energy detection circuit 13 is in the threshold range set by the threshold setting circuit.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An emission spectrophotometer, for generating a pulse light emission by supplying an energy accumulated in an electricity accumulating and discharging unit to a gap between an electrode and a test material, the emission spectrophotometer comprising:
    a first detection unit, for detecting an energy charged to the electricity accumulating and discharging unit before the pulse light emission; and
    a second detection unit, for detecting an energy remaining in the electricity accumulating and discharging unit after the pulse light emission;
    a comparison unit, generating a comparison result according to a comparison between the charged energy, detected before the pulse light emission, and a first preset threshold, and a comparison between the remaining energy, detected after the pulse light emission, and a second preset threshold;
    an output circuit; and
    a data processing device, wherein the output circuit outputs the comparison result to the data processing device.

2. The emission spectrophotometer according to claim 1, wherein:
    the electricity accumulating and discharging unit is a condenser.

3. The emission spectrophotometer according to claim 1, further comprising a threshold setting circuit, wherein the first preset threshold and the second preset threshold are set by the threshold setting circuit.

* * * * *